(12) United States Patent
Kobayashi et al.

(10) Patent No.: US 10,494,482 B2
(45) Date of Patent: Dec. 3, 2019

(54) PRODUCTION METHOD FOR ORGANOPOLYSILOXANE EMULSION COMPOSITION

(71) Applicant: SHIN-ETSU CHEMICAL CO., LTD., Tokyo (JP)

(72) Inventors: Akihiro Kobayashi, Annaka (JP); Yuko Takada, Annaka (JP); Shunji Aoki, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 88 days.

(21) Appl. No.: 15/757,533

(22) PCT Filed: Sep. 1, 2016

(86) PCT No.: PCT/JP2016/075662
§ 371 (c)(1),
(2) Date: Mar. 5, 2018

(87) PCT Pub. No.: WO2017/038936
PCT Pub. Date: Mar. 9, 2017

(65) Prior Publication Data
US 2018/0244850 A1    Aug. 30, 2018

(30) Foreign Application Priority Data

Sep. 4, 2015   (JP) ................. 2015-174330
Sep. 4, 2015   (JP) ................. 2015-174339

(51) Int. Cl.
C08G 77/08       (2006.01)
C08G 77/06       (2006.01)
C08G 77/04       (2006.01)
C08K 5/42        (2006.01)
C08L 83/04       (2006.01)
C08G 77/00       (2006.01)

(52) U.S. Cl.
CPC ........... *C08G 77/045* (2013.01); *C08G 77/06* (2013.01); *C08G 77/08* (2013.01); *C08G 77/70* (2013.01); *C08K 5/42* (2013.01); *C08L 83/04* (2013.01); *A61K 2800/21* (2013.01)

(58) Field of Classification Search
CPC .................................................. A61K 2800/21
See application file for complete search history.

(56) References Cited

U.S. PATENT DOCUMENTS 4,228,054 A    10/1980  Ona et al.
4,894,412 A    1/1990   Okada et al.
9,072,666 B2   7/2015   Ando 2007/0276087 A1*  11/2007  Paul ................. C08G 77/06
                                                        524/837
2014/0378553 A1   12/2014  Ando
2015/0037272 A1   2/2015   Ando
2015/0174049 A1*  6/2015   Rautschek ........... A61K 8/55
                                                        424/70.12
2015/0290091 A1*  10/2015  Ando ................. A61Q 5/02
                                                        424/401
2017/0174886 A1*  6/2017   Cauvin ............... C08L 83/04

FOREIGN PATENT DOCUMENTS

DE   10 2011 076 921 A1   12/2012
EP         2 706 080 A1   3/2014
(Continued)

OTHER PUBLICATIONS

International Search Report issued in PCT/JP2016/075662 (PCT/ISA/210), dated Oct. 4, 2016.
(Continued)

*Primary Examiner* — Marc S Zimmer
(74) *Attorney, Agent, or Firm* — Birch, Stewart, Kolasch & Birch, LLP

(57) ABSTRACT

A production method for an organopolysiloxane emulsion composition, wherein (I) an emulsion composition is prepared by emulsifying an organopolysiloxane (A) that is represented by formula (2), or that is a mixture of organopolysiloxanes represented by formulas (1) and (2), and that has an octamethylcyclotetrasiloxane content of 1000 ppm or less

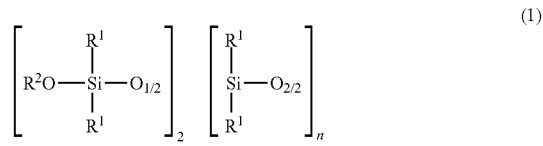

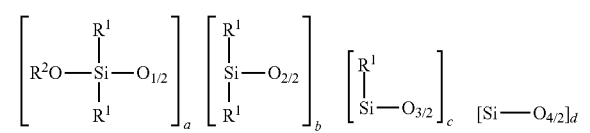

($R^1$ and $R^2$ are H or a monovalent hydrocarbon group, n is a number that makes the viscosity of the organopolysiloxane 200-100,000 mm$^2$/s, and a, b, c, and d satisfy the expressions a≥3, b≥5, c+d≥1, 10≤a+b+c+d≤1,000),
a surfactant (B), and
water (C-1), and
wherein (II) water (C-2) is added as needed and then emulsion polymerization is performed in the presence of an acid catalyst (D).
The organopolysiloxane generated has a 15 mass % toluene solution viscosity of 200 mPa·s or higher at 25° C., has an octamethylcyclotetrasiloxane content of 3000 ppm or less, and has a branched structure that has a particle size of 1 μm or less.

16 Claims, No Drawings

(56) References Cited

FOREIGN PATENT DOCUMENTS

| | | |
|---|---|---|
| JP | 56-38609 B2 | 9/1981 |
| JP | 63-286434 A | 11/1988 |
| JP | 2007-297533 A | 11/2007 |
| JP | 2012-201867 A | 10/2012 |
| JP | 5382273 B1 | 1/2014 |
| WO | WO 2013/153833 A1 | 10/2013 |
| WO | WO 2013/161500 A1 | 10/2013 |
| WO | WO 2014/084319 * | 5/2014 |
| WO | WO 2015/122989 A1 * | 8/2015 |

OTHER PUBLICATIONS

Written Opinion of the International Searching Authority issued in PCT/JP2016/075662 (PCT/ISA/237), dated Oct. 4, 2016.
Extended European Search Report dated Mar. 6, 2019, in European Patent Application No. 16841965.3.

* cited by examiner

PRODUCTION METHOD FOR ORGANOPOLYSILOXANE EMULSION COMPOSITION

TECHNICAL FIELD

The present invention relates to a method of producing emulsion compositions of high-viscosity organopolysiloxanes having a branched structure for use in products such as cosmetics, personal care compositions, home care compositions, mold release agents, slip agents, coating agents, textile finishes and resin modifiers.

BACKGROUND ART

There exists a desire for high-viscosity organopolysiloxanes which have a branched structure and are used in products such as cosmetics, personal care compositions, home care compositions, mold release agents, slip agents, coating agents, textile finishes and resin modifiers to be rendered into emulsions having a small particle size and a good stability over time. However, when a high-viscosity organopolysiloxane having a branched structure is directly emulsified, the lower limit in the size of the emulsion particles is about several microns; achieving a smaller particle size is difficult, and the resulting emulsion has a poor stability over time. Accordingly, various methods for producing emulsions of high-viscosity organopolysiloxanes having a branched structure by emulsion polymerization have been investigated in order to obtain emulsion particles with a good stability over time.

For example, methods for carrying out the emulsion polymerization of a cyclic siloxane oligomer and a trialkoxysilane in an emulsified state by using a strong acid or strong alkalinity are known (Patent Document 1: JP-B S56-038609; Patent Document 2: JP-A S63-286434). Using these methods, it is possible to obtain an emulsion having an emulsion particle size of 300 nm or less.

In recent years, there has come to be a desire for products in which the content of octamethylcyclotetrasiloxane is suppressed. In the methods described in Patent Documents 1 and 2, the organopolysiloxane included in the resulting emulsion is known to contain at least 40,000 ppm of octamethylcyclotetrasiloxane, and so methods for reducing this content are being investigated.

For example, methods are known wherein an organopolysiloxane which has a viscosity at 25° C. of from 3,000 to 100,000 mm$^2$/s and an octamethylcyclotetrasiloxane content of up to 1,000 ppm and which is capped at the ends of the molecular chain with silanol groups is emulsified, following which emulsion polymerization is carried out at a temperature below 40° C. and in the presence of an acid catalyst (Patent Document 3: JP No. 5382273). It is claimed that by using such a method, an emulsion in which the amount of octamethylcyclotetrasiloxane included in the organopolysiloxane is up to 3,000 ppm can be obtained. Mention is also made that by adding a trialkoxysilane to this emulsion, it is possible to introduce branched units onto the resulting organopolysiloxane chain. However, there exists the drawback that, even when a trialkoxysilane is reacted with a high-viscosity organopolysiloxane, due to a difference in reactivity between the organopolysiloxane capped at the ends of the molecule chain with silanol groups and the trialkoxysilane, branched units are not uniformly incorporated into the siloxane chain and so the viscosity of the organopolysiloxane chains that form does not increase.

Hence, there is a need to establish a method for producing an emulsion composition of a high-viscosity organopolysiloxane having a branched structure, which composition has a small particle size and a good stability over time, and which method suppresses the formation of octamethylcyclotetrasiloxane included in the organopolysiloxane as a by-product.

PRIOR ART DOCUMENTS

Patent Documents

Patent Document 1: JP-B S56-038609
Patent Document 2: JP-A S63-286434
Patent Document 3: JP No. 5382273

SUMMARY OF INVENTION

Technical Problem

It is therefore an object of this invention to provide a method for producing an emulsion composition of a high-viscosity organopolysiloxane having a branched structure, which composition has a small particle size and a good stability over time, and which method suppresses the formation of octamethylcyclotetrasiloxane included in the organopolysiloxane as a by-product.

Solution to Problem

The inventors have conducted extensive investigations in order to achieve these objects. As a result, they have discovered that by combining a linear organopolysiloxane having an octamethylcyclotetrasiloxane content of up to 1,000 ppm and a branched organopolysiloxane, or by using a branched organopolysiloxane alone, as the emulsion polymerization monomer, the amount of octamethylcyclotetrasiloxane included within the organopolysiloxane of an emulsion composition composed of a high-viscosity organopolysiloxane having a branched structure is 3,000 ppm or less, and the emulsion composition has a small particle size of up to 1 μm and a stability over time that is better than in the prior art. In this invention, the viscosity in mm$^2$/s units is the value at 25° C. as measured with an Ostwald viscometer.

Accordingly, the invention provides the following method for producing an organopolysiloxane emulsion composition.
[1] A method for producing an emulsion composition of an organopolysiloxane having a branched structure, the method comprising the steps of:
(I) preparing an emulsion composition by emulsifying a mixture comprising
(A) 100 parts by weight of an organopolysiloxane which is an organopolysiloxane of general formula (2) below or a mixture of organopolysiloxanes of general formula (1) and general formula (2) below and has an octamethylcyclotetrasiloxane content of up to 1,000 ppm

[Chem. 1]

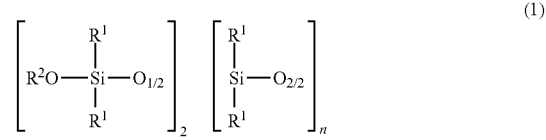

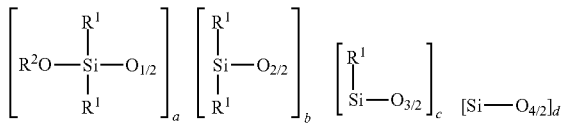

(wherein each $R^1$ and $R^2$ is independently a hydrogen atom or a substituted or unsubstituted monovalent hydrocarbon group of 1 to 20 carbon atoms; n is a number such that the organopolysiloxane has a viscosity at 25° C. of at least 200 mm²/s and up to 100,000 mm²/s; and a, b, c and d are each numbers which satisfy the conditions a≥3, b≥5, c+d≥1, and 10≤a+b+c+d≤1,000), (B) from 1 to 8 parts by weight of a surfactant, and (C-1) from 1 to 10,000 parts by weight of water; and (II) after optionally adding to the resulting emulsion composition (C-2) from 0 to 10,000 parts by weight of water, carrying out emulsion polymerization at a temperature below 40° C. in the presence of (D) an acid catalyst (addition of the acid catalyst may be omitted when the surfactant (B) has a catalytic action), wherein the formed organopolysiloxane has a 15 wt % toluene solution viscosity at 25° C. of at least 200 mPa·s, the amount of octamethylcyclotetrasiloxane included in the organopolysiloxane is up to 3,000 ppm, and the size of the resulting emulsion particles is up to 1 μm.

[2] The production method of [1], wherein n in general formula (1) or a, b, c and d in general formula (2) of component (A) are numbers such that the viscosity of the organopolysiloxane at 25° C. is at least 200 mm²/s and less than 2,000 mm²/s.

[3] The production method of [1], wherein n in general formula (1) and a, b, c and d in general formula (2) of component (A) are numbers such that the organopolysiloxane viscosity at 25° C. is at least 200 mm²/s and less than 2,000 mm²/s.

[4] The production method of any of [1] to [3], wherein an organopolysiloxane of general formula (2) alone is used as component (A) and the octamethylcyclotetrasiloxane content of this organopolysiloxane is up to 1,000 ppm.

[5] The production method of any of [1] to [4], wherein the surfactant (B) is an anionic surfactant.

[6] The production method of any of [1] to [4], wherein the surfactant (B) is an anionic surfactant and a nonionic surfactant.

[7] The production method of [5] or [6], wherein the anionic surfactant is a surfactant of general formula (3) below having an alkylnaphthalene skeleton $$R^3{}_m\text{—}C_{10}H_{(7-m)}\text{—}SO_3M \quad (3)$$

(wherein $R^3$ is a linear or branched alkyl group of 1 to 30 carbon atoms, M is a hydrogen ion, an alkali metal ion, an alkaline earth metal ion, an ammonium ion or a tertiary ammonium ion; and m is an integer from 1 to 3).

[8] The production method of any of [1] to [7] wherein, when the emulsion composition is prepared in Step (I) using an emulsifier that employs a high pressure to reduce the size of the emulsion particles, the amount of component (C-1) water used per 100 parts by weight of component (A) is from 1 to 10,000 parts by weight.

[9] The production method of any of [1] to [7] wherein, when the emulsion composition is prepared in Step (I) using an emulsifier that employs shear forces to reduce the size of the emulsion particles, the amount of component (C-1) water used per 100 parts by weight of component (A) is from 1 to 10 parts by weight.

[10] The production method of any of [1] to [9], wherein the amount of the acid catalyst of component (D) present (including, when the surfactant of component (B) has a catalytic action and is encompassed by the acid catalyst of component (D), the amount of the surfactant of component (B) present) is at least 0.1 part by weight per 100 parts by weight of component (A).

[11] The production method of any of [1] to [10] wherein, in Step (I), the particle size of the emulsion composition is set to up to 1 μm.

[12] The production method of any of [1] to [11], wherein the emulsion polymerization step is carried out at a temperature of below 25° C.

[13] The production method of any of [1] to [12], wherein the polymerization time in the emulsion polymerization step is up to 48 hours.

[14] The organopolysiloxane emulsion composition production method of any of [1] to [13], wherein the particles of the target emulsion composition have an average size of up to 800 nm.

[15] The organopolysiloxane emulsion composition production method of any of [1] to [12], wherein the organopolysiloxane in the target organopolysiloxane emulsion composition has a 15 wt % toluene solution viscosity at 25° C. of at least 300 mPa·s.

[16] The organopolysiloxane emulsion composition production method of any of [1] to [13], wherein the amount of octamethylcyclotetrasiloxane included in the organopolysiloxane within the target organopolysiloxane emulsion composition is up to 2,000 ppm.

Advantageous Effects of Invention

This invention makes it possible to obtain an emulsion composition of an organopolysiloxane having a branched structure and a 15 wt % toluene solution viscosity at 25° C. of at least 200 mPa·s, which composition has a good stability over time, an amount of octamethylcyclotetrasiloxane included in the organopolysiloxane of less than 3,000 ppm, and a particle size not larger than 1 μm.

DESCRIPTION OF EMBODIMENTS

The starting materials used in the production method of the invention are described below.

<(A) Organopolysiloxane>

The organopolysiloxane serving as component (A) of the invention is an organopolysiloxane of general formula (2) below or a mixture of organopolysiloxanes of general formula (1) and general formula (2) below, and has an octamethylcyclotetrasiloxane content of up to 1,000 ppm.

[Chem. 2]

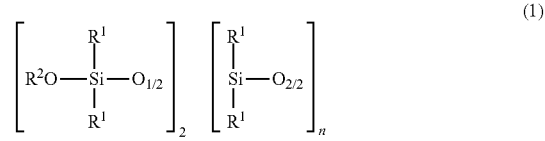

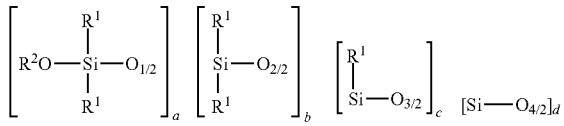

In the formulas, each $R^1$ and $R^2$ is independently a hydrogen atom or a substituted or unsubstituted monovalent hydrocarbon group of 1 to 20 carbon atoms; n is a number such that the organopolysiloxane viscosity at 25° C. is at least 200 mm²/s and up to 100,000 mm²/s; and a, b, c and d are each numbers which satisfy the conditions a≥3, b≥5, c+d≥1, and 10≤a+b+c+d≤1,000.

$R^1$ and $R^2$ are each independently a hydrogen atom or a substituted or unsubstituted monovalent hydrocarbon group of 1 to 20 carbon atoms. Unsubstituted monovalent hydrocarbon groups of 1 to 20 carbon atoms are exemplified by alkyl groups of 1 to 20 carbon atoms, cycloalkyl groups of 3 to 20 carbon atoms, alkenyl groups of 2 to 20 carbon atoms, aryl groups of 6 to 20 carbon atoms, and aralkyl groups of 7 to 20 carbon atoms. Illustrative examples include alkyl groups such as methyl, ethyl, propyl, butyl, pentyl, hexyl, heptyl, octyl, nonyl, decyl, dodecyl, tetradecyl, hexadecyl and octadecyl groups; cycloalkyl groups such as cyclopentyl and cyclohexyl groups; alkenyl groups such as vinyl, allyl and hexenyl groups; and aryl groups such as phenyl, tolyl and naphthyl groups. Substituted monovalent hydrocarbon groups of 1 to 20 carbon atoms are exemplified by the aforementioned monovalent hydrocarbon groups of 1 to 20 carbon atoms in which some of the hydrogen atoms are substituted with halogen atoms, amino groups, acryloxy groups, methacryloxy groups, epoxy groups, mercapto groups, carboxyl groups or hydroxyl groups. Preferred examples include monovalent hydrocarbon groups of 1 to 6 carbon atoms, such as methyl, ethyl, propyl, butyl and phenyl groups. The organopolysiloxane is even more preferably one in which at least 80% of all the R' groups are methyl groups. $R^2$ is preferably a hydrogen atom or an alkyl group of 1 to 18 carbon atoms, and more preferably a hydrogen atom or an alkyl group of 1 to 6 carbon atoms.

In general formula (1), n is a number such that the viscosity of the organopolysiloxane at 25° C. is at least 200 mm²/s and up to 100,000 mm²/s, and especially a number such that the viscosity is at least 200 mm²/s and less than 100,000 mm²/s. A number such that the viscosity is from 400 mm²/s to 50,000 mm²/s is preferred, a number such that the viscosity is from 600 mm²/s to 10,000 mm²/s is more preferred, and a number such that the viscosity is from 700 to 2,000 mm²/s is most preferred. At a viscosity below 200 mm²/s, in order to set the organopolysiloxane included in the target emulsion to the desired viscosity, there arises a need to length the emulsion polymerization time or an increase in the amount of octamethylcyclotetrasiloxane that forms as a by-product during emulsion polymerization. On the other hand, when the viscosity exceeds 100,000 mm²/s, a large amount of emulsifying agent is needed to make the particle size of the target emulsion obtained smaller.

In general formula (2), a, b, c and d are each numbers which satisfy the conditions a≥3, b≥5, c+d≥1, and 10≤a+b+c+d≤1,000.

In general formula (2), a, b, c and d are numbers such that the viscosity of the organopolysiloxane at 25° C. is at least 200 mm²/s and up to 100,000 mm²/s, preferably numbers such that the viscosity is from 400 mm²/s to 50,000 mm²/s, more preferably numbers such that the viscosity is from 600 mm²/s to 10,000 mm²/s, and most preferably numbers such that the viscosity is from 700 to 2,000 mm²/s. At a viscosity below 200 mm²/s, in order to set the organopolysiloxane included in the target emulsion to the desired viscosity, there arises a need to length the emulsion polymerization time or an increase in the amount of octamethylcyclotetrasiloxane that forms as a by-product during emulsion polymerization. On the other hand, when the viscosity exceeds 100,000 mm²/s, a large amount of emulsifying agent is needed to make the particle size of the target emulsion obtained smaller.

The octamethylcyclotetrasiloxane content in the organopolysiloxane of component (A) is preferably up to 1,000 ppm (by weight; the same applies below), and especially up to 500 ppm. The octamethylcyclotetrasiloxane content has no particular lower limit, and may even be 0 ppm.

As mentioned above, an organopolysiloxane of formula (2) may be used alone as component (A), or an organopolysiloxane of formula (1) and an organopolysiloxane of formula (2) may be used together in admixture as component (A). When organopolysiloxanes of formulas (1) and (2) are used in admixture, the usage ratio of the organopolysiloxane of formula (1) and the organopolysiloxane of formula (2), expressed as a weight ratio, is preferably from 99.9:0.1 to 0.1:99.9, and especially from 99:1 to 1:99.

Examples of organopolysiloxanes having the specific structure of component (A) of the invention include, but are not limited to, those shown below. In the formulas, Me, Et, Ph and OH stand for, respectively, methyl, ethyl, phenyl and hydroxyl groups.

[Chem. 3]

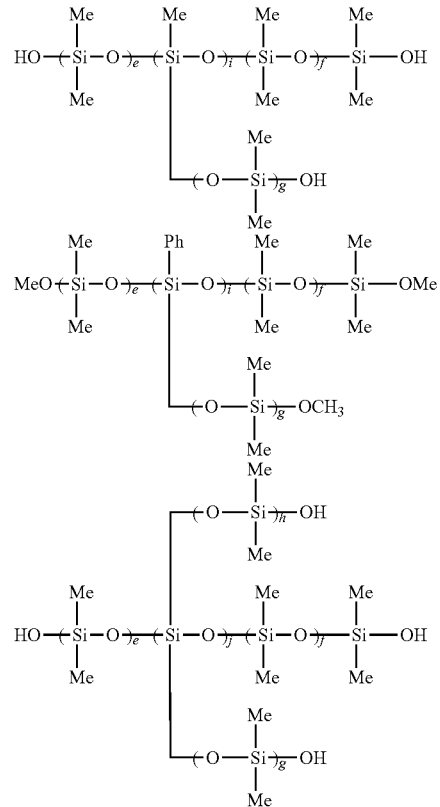

-continued

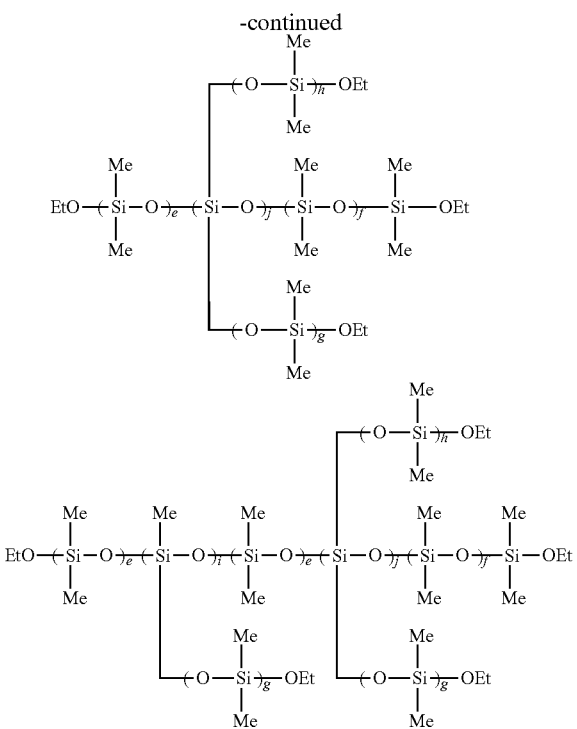

In these formulas, each of e, f, g, h, i and j is 1 or more and a number such that the viscosities of the above respective organopolysiloxanes have the above-indicated values.

<(B) Surfactant>

The surfactant serving as component (B) may be a single surfactant used alone or two or more surfactants may be suitably selected and used together. Of these, anionic surfactants and nonionic surfactants are preferred, with an anionic surfactant or the combined use of an anionic surfactant and a nonionic surfactants being especially preferred.

Examples of anionic surfactants include those mentioned below.

(1) Surfactants of General Formula (3) Below Having an Alkylnaphthalene Skeleton:

[Chem. 4]

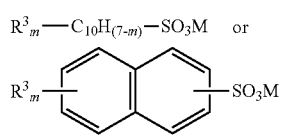   or

(3)

Here, $R^3$ is a linear or branched alkyl group of 1 to 30 carbon atoms, M is a hydrogen ion, an alkali metal ion such as potassium or sodium, an alkaline earth metal ion such as magnesium or calcium, an ammonium ion, or a tertiary ammonium ion such as a triethanolammonium ion. m is an integer from 1 to 3. Also, —$SO_3M$ generally bonds to the 1 position or 2 position on the naphthalene ring. The bonding position for $R^3$ is the 3 position, 4 position, 5 position, 6 position, 7 position or 8 position.

In general formula (3), $R^3$ is preferably a linear or branched alkyl group of 1 to 20 carbon atoms, and M is preferably, from the standpoint of the emulsifying effect, a sodium ion, a potassium ion, an ammonium ion or a triethanolammonium ion.

Examples of alkylnaphthalenesulfonic acids and salts thereof of general formula (3) include butylnaphthalenesulfonic acid, pentylnaphthalenesulfonic acid, decylnaphthalenesulfonic acid, dodecylnaphthalenesulfonic acid, tetradecylnaphthalenesulfonic acid, hexadecylnaphthalenesulfonic acid, isopropylnaphthalenesulfonic acid, bisisopropylnaphthalenesulfonic acid, trisisopropylnaphthalenesulfonic acid, and salts thereof (2) Alkylsulfuric Acids and Salts Thereof of General Formula (4) Below:

$$R^4OSO_3M \tag{4}$$

Here, $R^4$ is a linear or branched alkyl group of 6 to 30 carbon atoms; and M is a hydrogen ion, an alkali metal ion such as potassium or sodium, an alkaline earth metal ion such as magnesium or calcium, an ammonium ion, or a tertiary ammonium ion such as a triethanolammonium ion.

In general formula (4), $R^4$ is preferably a linear or branched alkyl group of 6 to 12 carbon atoms; and M is preferably, from the standpoint of the emulsifying effect, a sodium ion, a potassium ion, an ammonium ion or a triethanolammonium ion.

Specific examples of alkylsulfuric acids and salts thereof of general formula (4) include hexylsulfuric acid, octylsulfuric acid, decylsulfuric acid, dodecylsulfuric acid, tetradecylsulfuric acid, hexadecylsulfuric acid, octadecylsulfuric acid and eicosylsulfuric acid, lithium, sodium, potassium and other alkali metal salts thereof, magnesium, calcium and other alkaline earth metal salts thereof, and triethanolammonium salts and ammonium salts thereof.

(3) Alkylbenzenesulfonic Acids and Salts Thereof of General Formula (5) Below:

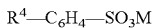 (5)

Here, $R^4$ is, as defined in general formula (4), a linear or branched alkyl group of 6 to 30 carbon atoms. M is, as defined in general formula (4), a hydrogen ion, an alkali metal ion such as potassium or sodium, an alkaline earth metal ion such as magnesium or calcium, an ammonium ion, or a tertiary ammonium ion such as a triethanolammonium ion.

In general formula (5), $R^4$ is preferably a linear or branched alkyl group of 6 to 12 carbon atoms; and M is preferably, from the standpoint of the emulsifying effect, a sodium ion, a potassium ion, an ammonium ion or a triethanolammonium ion.

Specific examples of alkylbenzenesulfonic acids and salts thereof of general formula (5) include hexylbenzenesulfonic acid, octylbenzenesulfonic acid, decylbenzenesulfonic acid, dodecylbenzenesulfonic acid, tetradecylbenzenesulfonic acid, hexadecylbenzenesulfonic acid, and salts thereof.

(4) Higher Fatty Acids and Salts Thereof:

Specific examples of higher fatty acids and salts thereof include lauric acid, stearic acid, oleic acid and linolenic acid, and their alkali metal salts such as lithium, sodium and potassium salts, alkaline earth metal salts such as magnesium and calcium salts, and triethanolammonium salts and ammonium salts.

(5) Polyoxyethylene Alkyl Ether Sulfuric Acids and Salts Thereof of General Formula (6) Below:

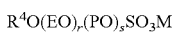 (6)

Here, $R^4$ is, as defined in general formula (4), a linear or branched alkyl group of 6 to 30 carbon atoms, and M is, as defined in general formula (4), a hydrogen ion, an alkali metal ion such as potassium or sodium, an alkaline earth metal ion such as magnesium or calcium, an ammonium ion, or a tertiary ammonium ion such as a triethanolammonium ion. EO represents an ethylene oxide group and PO represents a propylene oxide group, these being arranged randomly or as blocks. r and s are each independently integers from 0 to 100, with the proviso that r+s>0, and especially that 50≥r+s≥1.

Specific examples of polyoxyethylene alkyl ether sulfuric acids and salts thereof include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene hexadecyl ether sulfuric acid, polyoxyethylene octadecyl ether sulfuric acid and polyoxyethylene eicosyl ether sulfuric acid, and their alkali metal salts such as lithium, sodium and potassium salts, alkaline earth metal salts such as magnesium and calcium salts, and triethanolammonium salts and ammonium salts.

(6) Polyoxyethylene Alkyl Phenyl Ether Sulfuric Acids and Salts Thereof of General Formula (7) Below:

$$R^4—C_6H_4—O(EO)_r(PO)_sSO_3M \quad (7)$$

Here, $R^4$ is, as defined in general formula (4), a linear or branched alkyl group of 6 to 30 carbon atoms, and M is, as defined in general formula (4), a hydrogen ion, an alkali metal ion such as potassium or sodium, an alkaline earth metal ion such as magnesium or calcium, an ammonium ion, or a tertiary ammonium ion such as a triethanolammonium ion. EO, PO, r and s are as defined in general formula (6). That is, EO represents an ethylene oxide group and PO represents a propylene oxide group, these being arranged randomly or as blocks, and r and s are each independently integers from 0 to 100, with the proviso that r+s>0, and especially that 50≥r+s≥1.

Specific examples of polyoxyethylene alkyl phenyl ether sulfuric acids and salts thereof include polyoxyethylene hexyl phenyl ether sulfuric acid, polyoxyethylene octyl phenyl ether sulfuric acid, polyoxyethylene decyl phenyl ether sulfuric acid, polyoxyethylene dodecyl phenyl ether sulfuric acid, polyoxyethylene tetradecyl phenyl ether sulfuric acid, polyoxyethylene hexadecyl phenyl ether sulfuric acid, and their alkali metal salts such as lithium, sodium and potassium salts, alkaline earth metal salts such as magnesium and calcium salts, and triethanolammonium salts and ammonium salts.

Nonionic surfactants are exemplified by polyoxyalkylene alkyl ethers, polyoxyalkylene alkyl phenyl ethers, polyoxyethylene-polyoxypropylene alkyl ethers, polyoxyalkylene alkyl esters, polyoxyalkylene sorbitan alkyl esters, polyethylene glycols, polypropylene glycols and diethylene glycols. One type may be used alone, or two or more may be suitably selected and used together. Of these, nonionic surfactants of general formula (8) below are preferred.

$$R^5O(EO)_p(PO)_qH \quad (8)$$

Here, $R^5$ is a linear or branched alkyl group of 8 to 30 carbon atoms, EO represents an ethylene oxide group and PO represents a propylene oxide group, these being arranged randomly or as blocks. p and q are each independently integers from 0 to 100, with the proviso that p+q>0. In particular, in general formula (8) above, $R^5$ is preferably a linear or branched alkyl group of 8 to 13 carbon atoms and p and q are independently from 0 to 25, with 0<p+q≤50, and preferably 1≤p+q≤30.

Specific examples of nonionic surfactants of general formula (8) include polyoxyethylene octyl ether, polyoxyethylene-polyoxypropylene octyl ether, polyoxyethylene nonyl ether, polyoxyethylene decyl ether, polyoxyethylene-polyoxypropylene decyl ether, polyoxyethylene lauryl ether, polyoxyethylene-polyoxypropylene lauryl ether, polyoxyethylene tridecyl ether, polyoxyethylene-polyoxypropylene tridecyl ether and polyoxyethylene cetyl ether. Use can also be made of reactive surfactants having a functional group. These surfactants may be of one type used alone, or two or more may be used together. The alkyl group above may be linear or may be branched.

The amount of component (B) used per 100 parts by weight of component (A) may be set to from 1 to 8 parts by weight, and is preferably from 1.5 to 7.5 parts by weight, and more preferably from 2 to 7 parts by weight.

<(C) Water>

The water serving as component (C) is (C-1) used in Step (I) and, optionally, (C-2) used in Step (II).

In Step (I), the amount of water used as component (C-1) is from 1 to 10,000 parts by weight per 100 parts by weight of component (A), and varies according to the type of emulsifier used when reducing the size of the emulsion particles.

For example, in cases where a high-pressure homogenizer which uses high pressure to reduce the size of the emulsion particles is employed (e.g., an emulsifier which pressurizes a treatment liquid to a high or ultrahigh pressure and passes it through a slit to obtain shear forces, or an emulsifier which causes pressurized treatment liquids to obliquely collide with each other at ultrahigh speed and thereby atomize), the amount of component (C-1) used per 100 parts by weight of component (A) is preferably from 1 to 10,000 parts by weight, more preferably from 4 to 6,000 parts by weight, and even more preferably from 6 to 4,000 parts by weight.

Alternatively, in cases where an emulsifier such as a homogenizing disperser which uses shear forces to reduce the size of the emulsion particles (an emulsifier which causes a circular disk having saw-teeth on the outer periphery to rotate at high speed so as to obtain shear forces), a homogenizing mixer (an emulsifier having a stator installed on the outer periphery and a rotor installed at the interior that is made to rotate at high speed, thereby generating shear forces), or a colloid mill (an emulsifier in which the various ingredients are fed to a gap between a disk that rotates at high speed and a stationary disk, thereby generating shear forces) is employed, the amount of component (C-1) used per 100 parts by weight of component (A) is preferably from 1 to 10 parts by weight, more preferably from 2 to 8 parts by weight, and even more preferably from 4 to 6 parts by weight. Here, when more than 10 parts by weight is added, it may be difficult to obtain an emulsion composition in which the emulsion particles have a small size of 1 μm or less; when less that 1 part by weight is added, it may be difficult to obtain an oil-in-water (O/W) emulsion.

In Step (II), the water serving as component (C-2) may be added or may not be added, with the amount thereof preferably being up to 10,000 parts by weight (i.e., from 0 to 10,000 parts by weight) per 100 parts by weight of component (A). When component (C-2) is added, the amount thereof is preferably from 0.1 to 1,000 parts by weight, and more preferably from 1 to 500 parts by weight. It is generally preferable for the water serving as component (C-2) to be added when using an emulsifier such as a homogenizing disperser, a homogenizing mixer or a colloid mill.

<(D) Acid Catalyst>

When component (B) has a catalytic action (e.g., in cases where an acid from among the above anionic surfactants is used as component (B)), component (D) may be unnecessary. In cases where component (D) is used, a single type may be used alone or two or more may be suitably combined and used together.

Component (D) is exemplified by the following ingredients.

(1) Alkylsulfuric Acids of General Formula (9) Below and Alkylbenzenesulfonic Acids of General Formula (10) Below:

$$R^6OSO_3H \quad (9)$$

(wherein $R^6$ is a linear or branched alkyl group of 6 to 30 carbon atoms)

$$R^6-C_6H_4-SO_3H \quad (10)$$

(wherein $R^6$ is, as defined in general formula (9), a linear or branched alkyl group of 6 to 30 carbon atoms).

In above general formulas (9) and (10), $R^6$ is preferably a linear or branched alkyl group of 6 to 12 carbon atoms.

Specific examples of alkylsulfuric acids of general formula (9) include hexylsulfuric acid, octylsulfuric acid, decylsulfuric acid, dodecylsulfuric acid, tetradecylsulfuric acid, hexadecylsulfuric acid, octadecylsulfuric acid and eicosylsulfuric acid.

Specific examples of alkylbenzenesulfonic acids of general formula (10) include hexylbenzenesulfonic acid, octylbenzenesulfonic acid, decylbenzenesulfonic acid, dodecylbenzenesulfonic acid, tetradecylbenzenesulfonic acid and hexadecylbenzenesulfonic acid.

(2) Higher Fatty Acids:

Specific examples include lauric acid, stearic acid, oleic acid and linolenic acid.

(3) Polyoxyethylene Alkyl Ether Sulfuric Acids of General Formula (11) Below:

$$R^6O(EO)_t(PO)_uSO_3H \quad (11)$$

Here, $R^6$ is, as defined in general formula (9), a linear or branched alkyl group of 6 to 30 carbon atoms. EO represents an ethylene oxide group and PO represents a propylene oxide group, these being arranged randomly or as blocks. t and u are each independently integers from 0 to 100, with the proviso that t+u>0, and especially that 50 t+u 1.

Specific examples include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene hexadecyl ether sulfuric acid, polyoxyethylene octadecyl ether sulfuric acid and polyoxyethylene eicosyl ether sulfuric acid.

(4) Polyoxyethylene Alkyl Phenyl Ether Sulfuric Acids of General Formula (12) Below:

$$R^6-C_6H_4-O(EO)_t(PO)_uSO_3H \quad (12)$$

Here, $R^6$ is, as defined in general formula (9), a linear or branched alkyl group of 6 to 30 carbon atoms. EO, PO and t and u are as defined in general formula (11). That is, EO represents an ethylene oxide group and PO represents a propylene oxide group, these being arranged randomly or as blocks. t and u are each independently integers from 0 to 100, with the proviso that t+u>0, and especially that 50≥t+u≥1.

Specific examples include polyoxyethylene hexyl phenyl ether sulfuric acid, polyoxyethylene octyl phenyl ether sulfuric acid, polyoxyethylene decyl phenyl ether sulfuric acid, polyoxyethylene dodecyl phenyl ether sulfuric acid, polyoxyethylene tetradecyl phenyl ether sulfuric acid and polyoxyethylene hexadecyl phenyl ether sulfuric acid.

(5) Brønsted acids:

Examples include hydrochloric acid, hydrobromic acid, sulfuric acid, chlorosulfonic acid, phosphoric acid, orthophosphoric acid, metaphosphoric acid, polyphosphoric acid, boric acid, nitric acid, benzenesulfonic acid, methanesulfonic acid, trifluoromethanesulfonic acid, carboxylic acid, chloroacetic acid, trichloroacetic acid, acetic acid, acrylic acid, benzoic acid, trifluoroacetic acid, citric acid, crotonic acid, formic acid, fumaric acid, maleic acid, malonic acid, tannic acid, itaconic acid, lactic acid, tartaric acid, oxalic acid, phthalic acid, succinic acid, cation exchange resins, acidic zeolites, acid-active fuller's earth and acid-active carbon black.

The amount of component (D) used (that is, in cases where the surfactant serving as component (B) has a catalytic action (e.g., in cases where the surfactant is an acid for which, in the above formula, M is an oxygen atom) and is encompassed by the acid catalyst of component (D), the total amount including the amount of this component (B) used) is preferably at least 0.1 part by weight, more preferably at least 0.3 part by weight, and even more preferably at least 0.5 part by weight, per 100 parts by weight of component (A). When the amount is less than 0.1 part by weight, the polymerization rate may become extremely slow. The amount has no particular upper limit, although it is preferably up to 125 parts by weight.

The production method of the invention is described below.

<Step (I)>

An emulsion composition is prepared by emulsifying a mixture containing components (A), (B) and (C). Here, emulsification can be carried out using an emulsifier such as a homogenizing disperser, a homogenizing mixer, a colloid mill, a line mixer, a universal mixer, an ultra mixer, a planetary mixer, a combination mixer or a high-pressure homogenizer. An emulsifier which reduces the size of the emulsion particles using shear forces, such as a homogenizing disperser, a homogenizing mixer or a colloid mill, is preferred; a homogenizing disperser is even more preferred.

In this step, the emulsification temperature is preferably from 1 to 80° C. When component (B) has a catalytic action, a cyclization reaction also proceeds at the same time, and so emulsification is preferably carried out at a temperature of below 40° C. Should emulsification be carried out at a temperature of 40° C. or more, the production of octamethylcyclotetrasiloxane may increase. Accordingly, the temperature is preferably less than 30° C., and more preferably less than 25° C.

In Step (I), the mixture is mixed under the application of high shear forces until the size of the emulsion particles in the emulsion composition becomes preferably 1 μm or less, more preferably 800 nm or less, and even more preferably 600 nm or less. The smaller the size of the emulsion particles obtained in Step (I), the higher the rate of polymerization in Step (II), thus shortening the polymerization time. Because the size of the emulsion particles in the emulsion composition obtained in Step (I) is 500 nm or less, the ultimate size of the emulsion particles obtained in the next step is also 500 nm or less. In this invention, the size of the emulsion particles is the median diameter, as measured with a model LA-920 laser diffraction/scattering type particle size analyzer (Horiba, Ltd.).

<Step (II)>

After optionally adding and dispersing (C-2) water in the resulting emulsion composition, component (D) is optionally added at a temperature of below 40° C. And emulsion polymerization is carried out until the 15 wt % toluene solution viscosity at 25° C. of the organopolysiloxane becomes at least 200 mPa·s, as measured with a rotational viscometer.

In cases where component (C-2) has thus been added to the emulsion composition, emulsification/dispersion may be additionally carried out thereafter with an emulsifier such as a high-pressure homogenizer.

When the emulsion composition is emulsion polymerized, it is recommended that the polymerization step be carried out at a temperature of below 40° C. for up to 48 hours. When polymerization is carried out at a temperature above 40° C., octamethylcyclotetrasiloxane formation may increase. The polymerization temperature is thus preferably below 25° C., and more preferably below 15° C. When the polymerization time exceeds 48 hours, the formation of octamethylcyclotetrasiloxane as a by-product may increase. The polymerization time is thus preferably from 1 to 40 hours, and more preferably from 5 to 30 hours.

The organopolysiloxane produced by emulsion polymerization in step (II) has a 15 wt % toluene solution viscosity at 25° C., as measured with a rotational viscometer, of at least 200 mPa·s, preferably at least 300 mPa·s, more preferably at least 500 mPa·s, and most preferably at least 1,000 mPa·s. Although the viscosity is not subject to any particular upper limit, it is generally up to 100,000 mPa·s.

<Other Treatment>

Once polymerization has ended, the resulting emulsion composition is generally neutralized with a basic substance. Examples of the basic substance include sodium hydroxide, potassium hydroxide, sodium carbonate, sodium bicarbonate, and amine compounds such as triethanolamine and triethylamine.

The silicone concentration can be adjusted at this time by adding water. Also, additives such as preservatives and fungicides may be added in order to increase the shelf stability of the emulsion composition.

By adding an alkoxysilane such as $R^6_3Si(OR^7)$, $R^6_2Si(OR^7)_2$ or $R^6Si(OR^7)_3$ in Step (I) in which emulsification is carried out, in Step (II) in which emulsion polymerization is carried out, or to the emulsion composition after carrying out neutralization, various functional groups such as alkenyl, epoxy, amino, polyether, carbinol, mercapto, (meth)acrylic, carboxyl and fluorine groups can be introduced onto the resulting organopolysiloxane chain. Here, $R^6$ is a hydrogen atom or a substituted or unsubstituted monovalent hydrocarbon group of 1 to 20, and preferably 1 to 6, carbon atoms, illustrative examples of which include methyl, ethyl, propyl, butyl and phenyl groups. $R^7$ is the same or a different alkyl group of 1 to 20 carbon atoms or is a hydrogen atom.

In the emulsion composition which is obtained by the inventive method of production and includes an organopolysiloxane having a 15 wt % toluene solution viscosity at 25° C. of at least 200 mPa·s, the 15 wt % toluene solution viscosity of the organopolysiloxane in the emulsion composition is at least 200 mPa·s, preferably at least 300 mPa·s, and more preferably at least 500 mPa·s. Although the viscosity is not subject to any particular upper limit, it is generally up to 100,000 mPa·s.

The average size of the emulsion particles in the emulsion composition is preferably up to 1 μm, and more preferably up to 800 nm. Although not subject to any particular lower limit, the average particle size is generally at least about 30 nm. By way of this invention, a very fine emulsion composition in which the average size of the emulsion particles is up to 1 μm can be obtained. The average size of the emulsion particles is the median diameter obtained by a laser diffraction/scattering method.

The content of octamethylcyclotetrasiloxane included in the organopolysiloxane is up to 3,000 ppm, preferably up to 2,000 ppm, and more preferably up to 1,000 ppm. Although not subject to any particular lower limit, the content is 0 ppm or more.

The content of decamethylcyclopentasiloxane included in the organopolysiloxane is preferably up to 3,000 ppm, more preferably up to 2,000 ppm, and even more preferably up to 1,000 ppm. Although not subject to any particular lower limit, the content is 0 ppm or more.

EXAMPLES

The invention is illustrated more fully below by way of Examples and Comparative Examples, although these Examples are not intended to limit the invention. All references to "parts" are by weight. Viscosities are values measured at 25° C. with an Ostwald viscometer.

Example 1

6 parts of (B) sodium dodecylbenzenesulfonate and 16 parts of (C-1) water were mixed with 96.1 parts of (A) an organopolysiloxane having silanol groups at the ends of the molecular chain and a viscosity of 700 mm²/s (in general formula (1), $R^1$=methyl groups; octamethylcyclotetrasiloxane content, ≤50 ppm) and 3.9 parts of an organopolysiloxane having branched units (in general formula (2), $R^1$=methyl groups, $R^2$=methoxy groups, a=3, b=30, c=1 and d=0; octamethylcyclotetrasiloxane content, ≤50 ppm), and were emulsified with a homogenizing disperser. Next, 74.4 parts of (C-2) water was added to the resulting first emulsion and dilution/dispersion was carried out with a homogenizing mixer, following which emulsification/dispersion was carried out with a high-pressure homogenizer. Concentrated hydrochloric acid (C), 1.2 parts, was then added, and emulsion polymerization was carried out at 10° C. for 24 hours. This was followed by the addition of 2.4 parts of triethanolamine to the resulting emulsion and dilution/dispersion with a homogenizing mixer, thereby giving an emulsion composition. The results are shown in Table 1.

Example 2

3 parts of polyoxyethylene tridecyl ether (EO, 10 moles) and 4 parts of sodium dodecylbenzenesulfonate as component (B), and 5 parts of (C-1) water mixed with 57.2 parts of (A) an organopolysiloxane having silanol groups at the ends of the molecular chain and a viscosity of 1,500 mm²/s (in general formula (1), $R^1$=methyl groups; octamethylcyclotetrasiloxane content, ≤50 ppm) and 42.8 parts of an organopolysiloxane having branched units (in general formula (2), $R^1$=methyl groups, $R^2$=ethoxy groups, a=3, b=380, c=1 and d=0; octamethylcyclotetrasiloxane content, ≤50 ppm), and were emulsified with a homogenizing disperser. Next, 83.9 parts of (C-2) water was added to the resulting first emulsion and dilution/dispersion was carried out with a homogenizing mixer and 1.2 parts of (D) concentrated hydrochloric acid was subsequently added, following which emulsion polymerization was carried out at 10° C. for 21 hours. This was followed by the addition of 2.4 parts of triethanolamine to the resulting emulsion and dilution/dispersion with a homogenizing mixer, thereby giving an emulsion composition. The results are shown in Table 1.

Example 3

3 parts of polyoxyethylene tridecyl ether (EO, 10 moles) and 4 parts of sodium dodecylbenzenesulfonate as component (B), and 5 parts of (C-1) water mixed with 57.2 parts of (A) an organopolysiloxane having silanol groups at the ends of the molecular chain and a viscosity of 1,500 mm$^2$/s (in general formula (1), $R^1$=methyl groups; octamethylcyclotetrasiloxane content, ≤50 ppm) and 42.8 parts of an organopolysiloxane having branched units (in general formula (2), R'=methyl groups, $R^2$=ethoxy groups, a=4, b=380, c=0 and d=1; octamethylcyclotetrasiloxane content, ≤50 ppm), and were emulsified with a homogenizing disperser. Next, 84.4 parts of (C-2) water was added to the resulting first emulsion and dilution/dispersion was carried out with a homogenizing mixer and 0.6 parts of (D) concentrated hydrochloric acid was subsequently added, following which emulsion polymerization was carried out at 10° C. for 17 hours. This was followed by the addition of 2.4 parts of triethanolamine to the resulting emulsion and dilution/dispersion with a homogenizing mixer, thereby giving an emulsion composition. The results are shown in Table 1.

Example 4

7 parts of (B) dodecylbenzenesulfonic acid and 5 parts of (C-1) water were mixed with 100 parts of (A) an organopolysiloxane having branched units (in general formula (2), $R^1$=methyl groups, $R^2$=methoxy group, a=3, b=450, c=1, d=0; octamethylcyclotetrasiloxane content, ≤50 ppm), and emulsified with a homogenizing disperser. Next, 85 parts of (C-2) water was added to the resulting first emulsion and dilution/dispersion was carried out with a homogenizing mixer and 0.6 part of (D) concentrated hydrochloric acid was subsequently added, following which emulsion polymerization was carried out at 10° C. for 10 hours. This was followed by the addition of 3.8 parts of triethanolamine to the resulting emulsion and dilution/dispersion with a homogenizing mixer, thereby giving an emulsion composition. The results are shown in Table 1.

Example 5

5 parts of (B) sodium pentylnaphthalenesulfonate and 6 parts of (C-1) water were mixed with 96.1 parts of (A) an organopolysiloxane having silanol groups at the ends of the molecular chain and a viscosity of 700 mm$^2$/s (in general formula (1), $R^1$=methyl groups; octamethylcyclotetrasiloxane content, ≤50 ppm) and 3.9 parts of an organopolysiloxane having branched units (in general formula (2), $R^1$=methyl groups, $R^2$=methoxy groups, a=3, b=30, c=1 and d=0; octamethylcyclotetrasiloxane content, ≤50 ppm), and mulsified with a homogenizing disperser. Next, 85.4 parts of (C-2) water was added to the resulting first emulsion and dilution/dispersion was carried out with a homogenizing mixer. Concentrated hydrochloric acid (D), 1.2 parts, was subsequently added and emulsion polymerization was carried out at 10° C. for 11 hours. This was followed by the addition of 2.4 parts of triethanolamine to the resulting emulsion and dilution/dispersion with a homogenizing mixer, thereby giving an emulsion composition. The results are shown in Table 2.

Example 6

5 parts of (B) sodium trisisopropylnaphthalenesulfonate (in general formula (3), $R^3$ is an isopropyl group, M is a sodium ion, m=3) and 6 parts of (C-1) water were mixed with 57.2 parts of (A) an organopolysiloxane having silanol groups at the ends of the molecular chain and a viscosity of 1,500 mm$^2$/s (in general formula (1), $R^1$=methyl groups; octamethylcyclotetrasiloxane content, ≤50 ppm) and 42.8 parts of an organopolysiloxane having branched units (in general formula (2), $R^1$=methyl groups, $R^2$=ethoxy groups, a=4, b=380, c=0 and d=1; octamethylcyclotetrasiloxane content, ≤50 ppm), and emulsified with a homogenizing disperser. Next, 86 parts of (C-2) water was added to the resulting first emulsion and dilution/dispersion was carried out with a homogenizing mixer. Concentrated hydrochloric acid (D), 0.6 part, was subsequently added and emulsion polymerization was carried out at 10° C. for 7 hours. This was followed by the addition of 2.4 parts of triethanolamine to the resulting emulsion and dilution/dispersion with a homogenizing mixer, thereby giving an emulsion composition. The results are shown in Table 2.

Example 7

5 parts of (B) sodium trisisopropylnaphthalenesulfonate (in general formula (3), $R^3$ is an isopropyl group, M is a sodium ion, m=3) and 6 parts of (C-1) water were mixed with 57.2 parts of (A) an organopolysiloxane having silanol groups at the ends of the molecular chain and a viscosity of 1,500 mm$^2$/s (in general formula (1), $R^1$=methyl groups; octamethylcyclotetrasiloxane content, ≤50 ppm) and 42.8 parts of an organopolysiloxane having branched units (in general formula (2), $R^1$=methyl groups, $R^2$=ethoxy groups, a=4, b=380, c=0 and d=1; octamethylcyclotetrasiloxane content, ≤50 ppm), and emulsified with a homogenizing disperser. Next, 86 parts of (C-2) water was added to the resulting first emulsion and dilution/dispersion was carried out with a homogenizing mixer. Concentrated hydrochloric acid (D), 0.6 part, was subsequently added, and emulsion polymerization was carried out at 10° C. for 6 hours. This was followed by the addition of 2.4 parts of triethanolamine to the resulting emulsion and dilution/dispersion with a homogenizing mixer, thereby giving an emulsion composition. The results are shown in Table 2.

Example 8

5 parts of (B) pentylnaphthalenesulfonic acid (in general formula (3), $R^3$ is a methyl group, M is a hydrogen atom, m=1) and 6 parts of (C-1) water were mixed with 100 parts of (A) an organopolysiloxane having branched units (in general formula (2), R'=methyl groups, $R^2$=methoxy groups, a=3, b=450, c=1 and d=0; octamethylcyclotetrasiloxane content, ≤50 ppm), and emulsified with a homogenizing disperser. Next, 85.8 parts of (C-2) water was added to the resulting first emulsion, dilution/dispersion was carried out with a homogenizing mixer, and emulsion polymerization was subsequently carried out at 10° C. for 4 hours. This was followed by the addition of 3.2 parts of triethanolamine to the resulting emulsion and dilution/dispersion with a homogenizing mixer, thereby giving an emulsion composition. The results are shown in Table 2.

Comparative Example 1

6 parts of (B) sodium dodecylbenzenesulfonate and 16 parts of (C-1) water were mixed with 99.73 parts of an organopolysiloxane having silanol groups at the ends of the molecular chain and a viscosity of 700 mm$^2$/s (in general formula (1), R$^1$=methyl groups; octamethylcyclotetrasiloxane content, ≤50 ppm) and 0.27 part of methyltriethoxysilane, and emulsified with a homogenizing disperser. Next, 74.4 parts of (C-2) water was added to the resulting first emulsion, dilution/dispersion was carried out with a homogenizing mixer, and emulsification/dispersion was subsequently carried out with a high-pressure homogenizer. Next, 1.2 parts of (D) concentrated hydrochloric acid was added and emulsion polymerization was carried out at 10° C. for 24 hours. This was followed by the addition of 2.4 parts of triethanolamine to the resulting emulsion and dilution/dispersion with a homogenizing mixer, thereby giving an emulsion composition. The results are shown in Table 1.

Comparative Example 2

3 parts of (B) polyoxyethylene tridecyl ether (EO, 10 moles), 4 parts of sodium dodecylbenzenesulfonate and 5 parts of (C-1) water were mixed with 99.64 parts of an organopolysiloxane having silanol groups at the ends of the molecular chain and a viscosity of 1,500 mm$^2$/s (in general formula (1), R$^1$=methyl groups; octamethylcyclotetrasiloxane content, ≤50 ppm) and 0.36 part of phenyltriethoxysilane, and emulsified with a homogenizing disperser. Next, 84.4 parts of (C-2) water was added to the resulting first emulsion, dilution/dispersion was carried out with a homogenizing mixer and 1.2 parts of (D) concentrated hydrochloric acid was subsequently added, following which emulsion polymerization was carried out at 10° C. for 24 hours. This was followed by the addition of 2.4 parts of triethanolamine to the resulting emulsion and dilution/dispersion with a homogenizing mixer, thereby giving an emulsion composition. The results are shown in Table 1.

The following properties of the emulsion compositions obtained in the above Examples were measured or evaluated by the methods shown below. The results are shown in Table 1.

[Average Particle Size of Emulsion]

This is the median diameter, as measured with a model LA-920 laser diffraction/scattering type particle size analyzer (Horiba, Ltd.).

[Viscosity of Organopolysiloxane]

Isopropyl alcohol, 300 g, was added under stirring to 300 g of the prepared emulsion composition. Only the organopolysiloxane that separated out was collected and dried at 105° C. for 3 hours and then dissolved in toluene, following which the viscosity at 25° C. was measured with a rotational viscometer. This is the 15 wt % toluene solution viscosity at 25° C.

[Octamethylcyclotetrasiloxane Content in Organopolysiloxane]

The emulsion composition, 0.1 g, was extracted (3 hours of shaking) with 10 mL of acetone containing 20 ppm (weight basis) of tetradecane as an internal standard and then left to stand overnight, following which the acetone layer was collected and the octamethylcyclotetrasiloxane was quantitatively determined by gas chromatographic analysis.

[Stability of Emulsion]

The emulsion composition, 100 g, was placed in a 100 mL glass jar and left to stand for three months at 50° C., following which the appearance was examined. When the emulsion formed a single uniform phase and no separation was observable, the stability was rated as "◯." When even a little separation into two phases was observed, the stability was rated as "x."

TABLE 1

| | Polymerization temperature (° C.) | Polymerization time (hr) | Average particle size (nm) | 15 wt % Toluene solution viscosity (mPa · s) | D$_4$ content (ppm) | Stability (50° C., 3 months) |
|---|---|---|---|---|---|---|
| Example 1 | 10 | 24 | 450 | 500 | 1,500 | ◯ |
| Example 2 | 10 | 21 | 180 | 1,200 | 1,000 | ◯ |
| Example 3 | 10 | 17 | 190 | 1,250 | 900 | ◯ |
| Example 4 | 10 | 10 | 220 | 1,400 | 750 | ◯ |
| Comparative Example 1 | 10 | 24 | 450 | 160 | 5,400 | X |
| Comparative Example 2 | 10 | 24 | 190 | 130 | 4,500 | X |

Note:
D$_4$: Octamethylcyclotetrasiloxane

TABLE 2

| | Polymerization temperature (° C.) | Polymerization time (hr) | Average particle size (nm) | 15 wt % Toluene solution viscosity (mPa · s) | D$_4$ content (ppm) | Stability (50° C., 3 months) |
|---|---|---|---|---|---|---|
| Example 5 | 10 | 11 | 200 | 1,200 | 550 | ◯ |
| Example 6 | 10 | 7 | 210 | 1,200 | 400 | ◯ |
| Example 7 | 10 | 6 | 210 | 1,250 | 380 | ◯ |
| Example 8 | 10 | 4 | 190 | 1,600 | 400 | ◯ |

Note:
D$_4$: Octamethylcyclotetrasiloxane

INDUSTRIAL APPLICABILITY

The inventive composition has an excellent stability and is very pleasant to use, making it particularly useful for cosmetics and household goods. For example, it can be used in hair care products such as shampoos and rinses.

It can also be used as a protective material for furniture and sundry articles, as a coating agent for rubber, plastic, concrete, mortar, wood and paper, as a mold release agent for molds used when manufacturing rubber products and plastic products, and as a textile finish for imparting water repellency and softness to fibers.

The invention claimed is:

1. A method for producing an emulsion composition of an organopolysiloxane having a branched structure, the method comprising the steps of:
   (I) preparing an emulsion composition by emulsifying a mixture comprising
      (A) 100 parts by weight of an organopolysiloxane which is an organopolysiloxane of general formula (2) below or a mixture of organopolysiloxanes of general formula (1) and general formula (2) below and has an octamethylcyclotetrasiloxane content of up to 1,000 ppm

[Chem. 1]

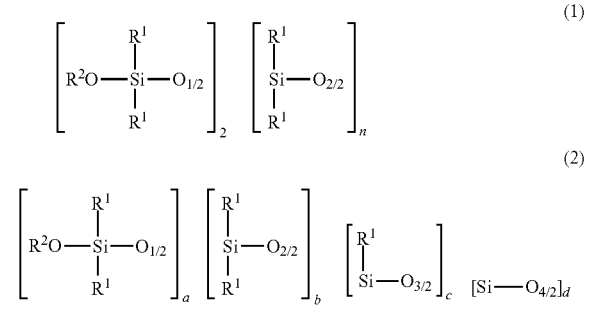

(wherein each $R^1$ and $R^2$ is independently a hydrogen atom or a substituted or unsubstituted monovalent hydrocarbon group of 1 to 20 carbon atoms; the subscript n is a number such that the organopolysiloxane has a viscosity at 25° C. of at least 200 mm²/s and up to 100,000 mm²/s; and the subscripts a, b, c and d are each numbers which satisfy the conditions $a \geq 3$, $b \geq 5$, $c+d \geq 1$, and $10 \leq a+b+c+d \leq 1,000$),
   (B) from 1 to 8 parts by weight of a surfactant, and
   (C-1) from 1 to 10,000 parts by weight of water; and
   (II) after optionally adding to the resulting emulsion composition
   (C-2) from 0 to 10,000 parts by weight of water, carrying out emulsion polymerization at a temperature below 40° C. in the presence of
      (D) an acid catalyst (addition of the acid catalyst may be omitted when the surfactant (B) has a catalytic action),
   wherein the formed organopolysiloxane has a 15 wt % toluene solution viscosity at 25° C. of at least 200 mPa·s, the amount of octamethylcyclotetrasiloxane included in the organopolysiloxane is up to 3,000 ppm, and the size of the resulting emulsion particles is up to 1 μm.

2. The production method of claim 1, wherein the subscript n in general formula (1) or the subscripts a, b, c and d in general formula (2) of component (A) are numbers such that the viscosity of the organopolysiloxane at 25° C. is at least 200 mm²/s and less than 2,000 mm²/s.

3. The production method of claim 1, wherein the subscript n in general formula (1) and the subscripts a, b, c and d in general formula (2) of component (A) are numbers such that the organopolysiloxane viscosity at 25° C. is at least 200 mm²/s and less than 2,000 mm²/s.

4. The production method of claim 1, wherein an organopolysiloxane of general formula (2) alone is used as component (A) and the octamethylcyclotetrasiloxane content of this organopolysiloxane is up to 1,000 ppm.

5. The production method of claim 1, wherein the surfactant (B) is an anionic surfactant.

6. The production method of claim 1, wherein the surfactant (B) is an anionic surfactant and a nonionic surfactant.

7. The production method of claim 5, wherein the anionic surfactant is a surfactant of general formula (3) below having an alkylnaphthalene skeleton

(wherein $R^3$ is a linear or branched alkyl group of 1 to 30 carbon atoms, M is a hydrogen ion, an alkali metal ion, an alkaline earth metal ion, an ammonium ion or a tertiary ammonium ion; and m is an integer from 1 to 3).

8. The production method of claim 1 wherein, when the emulsion composition is prepared in Step (I) using an emulsifier that employs a high pressure to reduce the size of the emulsion particles, the amount of component (C-1) water used per 100 parts by weight of component (A) is from 1 to 10,000 parts by weight.

9. The production method of claim 1 wherein, when the emulsion composition is prepared in Step (I) using an emulsifier that employs shear forces to reduce the size of the emulsion particles, the amount of component (C-1) water used per 100 parts by weight of component (A) is from 1 to 10 parts by weight.

10. The production method of claim 1, wherein the amount of the acid catalyst of component (D) present (including, when the surfactant of component (B) has a catalytic action and is encompassed by the acid catalyst of component (D), the amount of the surfactant of component (B) present) is at least 0.1 part by weight per 100 parts by weight of component (A).

11. The production method of claim 1 wherein, in Step (I), the particle size of the emulsion composition is set to up to 1 μm.

12. The production method of claim 1, wherein the emulsion polymerization step is carried out at a temperature of below 25° C.

13. The production method of claim 1, wherein the polymerization time in the emulsion polymerization step is up to 48 hours.

14. The organopolysiloxane emulsion composition production method of claim 1, wherein the particles of the target emulsion composition have an average size of up to 800 nm.

15. The organopolysiloxane emulsion composition production method of claim 1, wherein the organopolysiloxane in the target organopolysiloxane emulsion composition has a 15 wt % toluene solution viscosity at 25° C. of at least 300 mPa·s.

16. The organopolysiloxane emulsion composition production method of claim 1, wherein the amount of octamethylcyclotetrasiloxane included in the organopolysiloxane within the target organopolysiloxane emulsion composition is up to 2,000 ppm.

* * * * *